United States Patent
Fabrizio et al.

(10) Patent No.: US 6,745,311 B2
(45) Date of Patent: Jun. 1, 2004

(54) METHOD OF ALLOCATING CLUSTERS OF COMPUTER READABLE MEDIUM TO A FILE WHILE MINIMIZING FRAGMENTATION OF THE COMPUTER READABLE MEDIUM

(75) Inventors: Daniel Fabrizio, Dix Hills, NY (US); Jonathan Daub, New York, NY (US)

(73) Assignee: Networks Associates Technology, Inc., Santa Clara, CA (US)

( * ) Notice: Subject to any disclaimer, the term of this patent is extended or adjusted under 35 U.S.C. 154(b) by 609 days.

(21) Appl. No.: 09/768,517

(22) Filed: Jan. 24, 2001

(65) Prior Publication Data

US 2002/0138505 A1 Sep. 26, 2002

(51) Int. Cl.$^7$ .............................................. G06F 12/00
(52) U.S. Cl. ........................................ 711/172; 707/205
(58) Field of Search ................................. 711/170, 171, 711/172, 173; 707/205

(56) References Cited

U.S. PATENT DOCUMENTS

| | | | | | |
|---|---|---|---|---|---|
| 5,991,776 A | * | 11/1999 | Bennett et al. | ............. | 707/205 |
| 6,031,698 A | * | 2/2000 | Bar | ............................ | 360/134 |
| 6,185,665 B1 | * | 2/2001 | Owada et al. | .............. | 711/170 |

* cited by examiner

*Primary Examiner*—Hiep T. Nguyen
(74) *Attorney, Agent, or Firm*—Silicon Valley IP Group, PC; Kevin J. Zilka; Christopher J. Hamaty

(57) ABSTRACT

The present invention is a method of allocating clusters of a disk or other computer readable medium containing a plurality of clusters to minimize fragmentation. To accomplish this, at least one available block is identified in the computer readable medium. Each block includes one or more contiguous available clusters, where each cluster comprises one or more units of storage space. A request is received to allocate one or more clusters to a file. At least one of the available blocks is selected based on a location of the available block. At least some of the clusters are allocated, and the file is written to the allocated clusters.

71 Claims, 4 Drawing Sheets

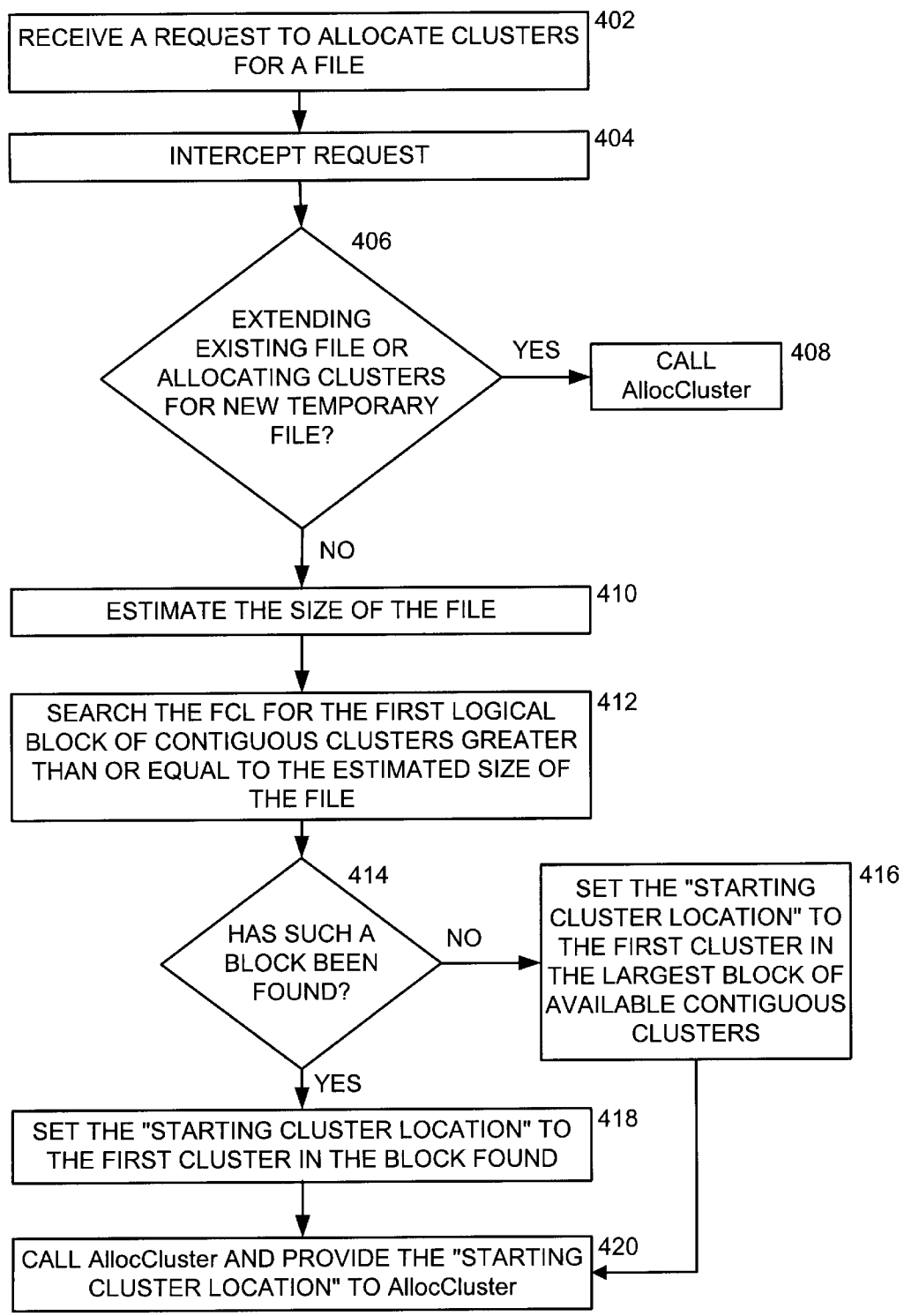

METHOD OF ALLOCATING CLUSTERS OF COMPUTER READABLE MEDIUM TO A FILE WHILE MINIMIZING FRAGMENTATION OF THE COMPUTER READABLE MEDIUM

FIELD OF THE INVENTION

The present invention relates to a method of minimizing disk fragmentation in real-time.

BACKGROUND OF THE INVENTION

Current computer systems typically include a hard disk or some other type of computer readable medium (hereinafter collectively referred to as a "disk"). The storage space in a disk is segmented into fixed size data areas known as sectors. The file system of the computer system typically groups the disk sectors into fixed or variable size areas known as clusters. A cluster is a group of one or more disk sectors. Clusters of a disk on computers running Microsoft Windows 95® may be, for example, 8 or 16 kilobytes in size. Each cluster is assigned a unique identifier (hereinafter referred to as a "cluster ID"). The cluster IDs are typically assigned sequentially starting with the innermost cluster of a disk.

Each file and directory stored on the disk is contained in one or more clusters. Unallocated clusters represent the free space on the disk. Contiguous unallocated clusters represent a single block of free space (an "available block"). Unallocated clusters which are surrounded by allocated clusters represent isolated blocks of free space on the disk.

The location of files stored on a disk are typically included in an allocation table or the like. An allocation table generally includes at least one file identifier and a corresponding list of the cluster IDs in which each file is stored. The operating system running on the computer is responsible for creating and updating the allocation table. For instance, when a file is created, the operating system updates the allocation table to specify the clusters which are allocated to that file. When a file is deleted, the allocation table is updated to indicate that the clusters previously allocated to that file are now available.

Operating systems, including Microsoft Windows 95®, Windows 98®, and Windows ME® (Millenium Edition), allocate space for new files beginning at the first available cluster, i.e., the cluster with the lowest cluster ID which is available. For files which are being extended and the last cluster allocated to the file has cluster ID N, space is allocated at the first available cluster after cluster ID N. While this method of allocating space for new files is fast, it often results in fragmented files and many small isolated blocks. This methodology does not attempt to ensure that the clusters to be allocated to a file are contiguous. However, if the total size of the disk is substantially larger than the files it contains, there is a large amount of free space on the disk, which is frequently consolidated into a single large block of free space.

Fragmentation occurs when a file is stored in noncontiguous clusters. In general, it is desirable to avoid fragmentation of a file. First, reading and writing fragmented files involves more discrete input/output operations than for similar contiguous (unfragmented) files. Second, an input/output operation to a contiguous file on a disk is usually much faster than any number of smaller discrete input/output operations to a fragmented file. Third, if the discontiguous clusters are physically far apart, the seek time to find each fragmented cluster may be substantial. Fourth, fragmented files limit the effectiveness of read ahead caching. Fifth, fragmentation often causes more fragmentation of the disk as new files are written.

While there are many defragmentation programs currently on the market, they only defragment the disk when the program is run and are not real-time. Since most users only sporadically run such defragmentation programs, there is a continuing need for real-time methods for minimizing fragmentation.

SUMMARY OF THE INVENTION

The present invention is a method of allocating clusters of a disk or other computer readable medium containing a plurality of clusters to minimize fragmentation.

The method includes the steps of (a) identifying at least one available block in the computer readable medium, each block including one or more contiguous available clusters; (b) determining the size, location, or both of at least one identified block; (c) receiving a request to allocate one or more clusters to a file; (d) determining a starting cluster location based on the size of at least one of the identified available blocks, the location of at least one of the identified available blocks, or both; and (e) allocating the clusters requested beginning at the starting cluster location. Generally, the starting cluster location is not determined from only the location of one available block. Steps (a)–(d) may be performed in any order and may even be performed concurrently. Steps (a) and (b) are preferably performed concurrently and more preferably before step (d). Steps (a) and (b) are also preferably performed before step (c). According to a preferred embodiment, step (d) includes (i) determining or estimating the size, type, name, location (if the file already exists), or combination thereof of the file; and (ii) determining a starting cluster location based on the estimated size, type, name, location, or combination thereof of the file and the size, location, or both of at least one block. The method can also include the step of(f) identifying the allocated clusters as being unavailable.

By determining or estimating the size of the file for which storage space is to be allocated, a block of contiguous clusters close in size to the file may be chosen. This results in minimal fragmentation of the file. In contrast, in the prior art method, the first available cluster with the lowest cluster ID would be chosen, even if the following cluster was not available.

The name and type of the file can be used to determine or estimate the longevity of the file. Short lived files can be placed in remote unused areas of the computer readable medium in order to minimize fragmentation.

Alternatively, an available block near a specific location on the computer readable medium may be chosen in step (d) in order to minimize the seek time required to retrieve information. For example, if a request to extend a preexisting file is received, a starting cluster location may be chosen which is physically closest to the clusters allocated to the preexisting file. Unlike the prior art method, which only searches for the first available cluster after the last cluster allocated to a file, the method of the present invention can determine the closest available cluster before or after the clusters allocated to the preexisting file. The starting cluster location may also be determined based on the closest available block which has a size greater than or equal to an estimated size of the file. If a new file is being created, a starting cluster location closest to the current physical position of the drive head can be chosen.

According to a preferred embodiment, the method includes the steps of (a) identifying at least one available block in the computer readable medium, each block including one or more contiguous available clusters; (b) determining the size, location, or both of at least one of the identified available blocks; (c) receiving a request to allocate one or more clusters to a file; (d) identifying the largest available block on the computer readable medium; (e) selecting a starting cluster location within the largest available block; and (f) allocating the clusters requested beginning at the starting cluster location.

According to another preferred embodiment, the method includes the steps of (a) identifying at least one available block in the computer readable medium, each block including one or more contiguous available clusters; (b) determining the size, location, or both of at least one of the identified available blocks; (c) receiving a request to allocate one or more clusters to a file; (d) determining the type, name, location, or combination thereof of the file; (e) determining a starting cluster location based on (i) the type, name, location, or combination thereof of the file and (ii) the size of at least one of the identified available blocks, the location of at least one of the identified available blocks, or both; and (f) allocating the clusters requested beginning at the starting cluster location.

According to yet another preferred embodiment, the method includes the steps of (a) identifying at least one available block in the computer readable medium, each block including one or more contiguous available clusters; (b) determining the size and location of each identified available block; (c) intercepting or receiving a request to allocate one or more clusters to a file; (d) determining or estimating the size of the file; (e) determining a starting cluster location based on the estimated size of the file and the size of at least one available block; and (f) allocating the clusters requested beginning at the starting cluster location. According to one embodiment, the size of the block represents the number of contiguous available clusters.

In one embodiment, the size of the file is estimated by assuming it is a predetermined size, such as 1 or 4 megabytes, or the sum of the predetermined size and the size of the space requested (in step (c)).

According to yet another preferred embodiment, the method includes the steps of (a) identifying at least one available block in the computer readable medium, each block including one or more contiguous available clusters; (b) determining the size, location, or both of at least one of the identified available blocks; (c) receiving a request to allocate one or more clusters to a file; (d) identifying a location on the computer readable medium; (e) determining a starting cluster location based on (i) the identified location and (ii) the location of at least one of the identified available blocks; and (f) allocating the clusters requested beginning at the starting cluster location.

According to yet another preferred embodiment, (a) identifying at least one available block in the computer readable medium, each block including one or more contiguous available clusters; (b) determining the size, location, or both of at least one of the identified available blocks; (c) intercepting a request to a Windows operating system routine to allocate one or more clusters to a file; (d) determining a starting cluster location based on the size of at least one of the identified available blocks, the location of at least one of the identified available blocks, or both; and (e) sending a request to the Windows operating system routine to allocate one or more clusters to the file beginning at the starting cluster location. The file system of the computer readable medium is preferably FAT or FAT32.

Yet another embodiment is a computer readable medium containing a software program that includes instructions for performing any of the methods of the present invention.

The invention also includes a computer system comprising (a) a computer readable medium having a plurality of clusters; and (b) a processor in communication with the computer readable medium. The processor is configured to perform any of the methods of the present invention.

BRIEF DESCRIPTION OF THE DRAWINGS

The foregoing and other features of the present invention will be more readily apparent from the following detailed description and drawings of the illustrative embodiments of the invention in which:

FIG. 4 is a flow chart of a preferred method for minimizing fragmentation of the invention.

DETAILED DESCRIPTION OF THE INVENTION

The term "file" as used herein includes any block of information stored on a computer readable medium including, but not limited to, directories and files.

The term "cluster" as used herein is defined as one or more fixed or variable size units of storage space. Typically, a cluster is a group of one or more disk sectors of the computer readable medium.

The term "Windows operating system routine" as used herein is defined as any operating system routine in any Microsoft Windows® operating system, including, but not limited to, Microsoft Windows 95®, Windows 98®, Windows ME®, Windows NT®, and Windows 2000® (Standard and Professional Edition), such as those included in the vmm.vxd and vfat.vxd drivers of Microsoft Windows 95® and Windows 98® (e.g. the ExecInt routine).

Figure 1:
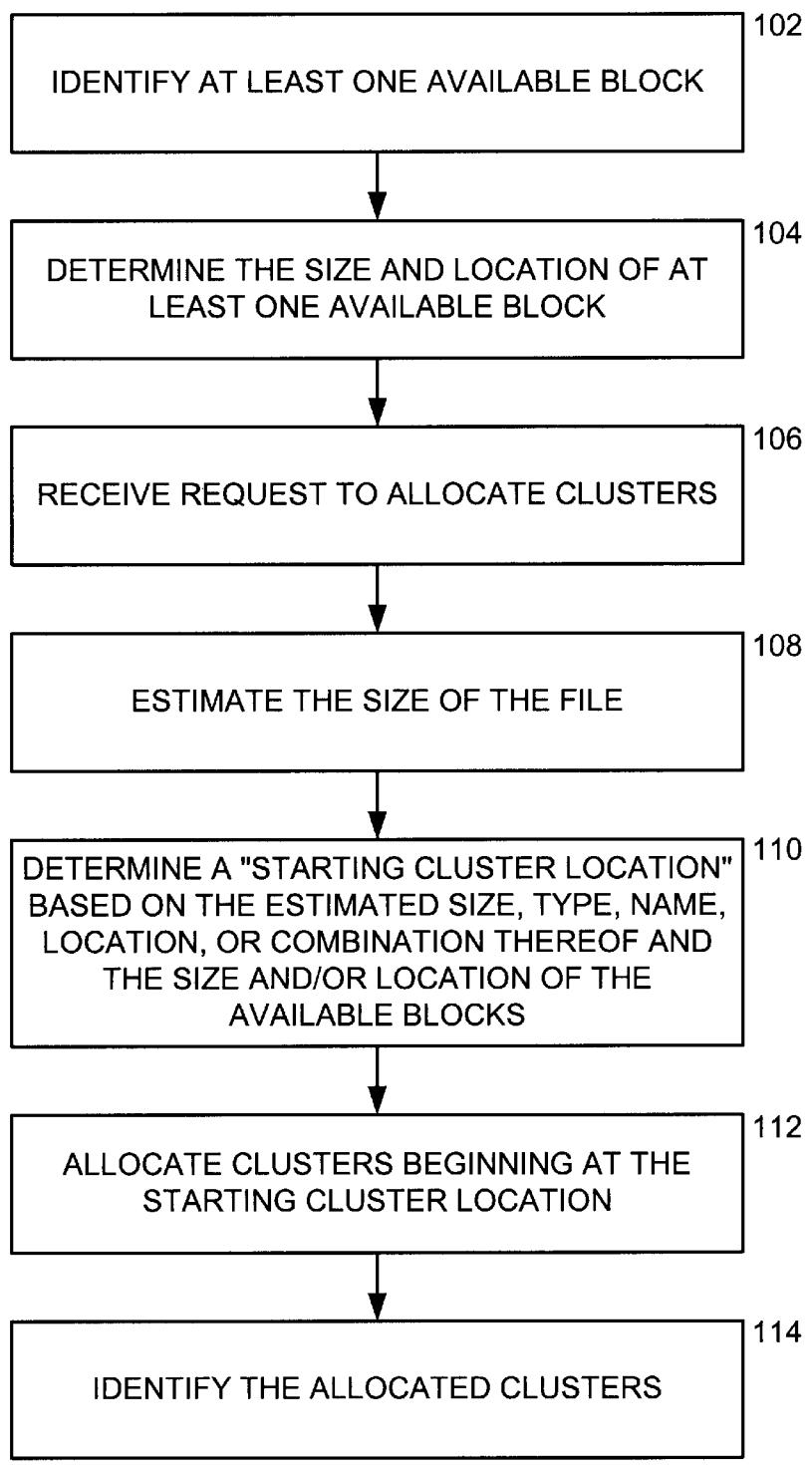
FIG. 1 is a flow chart of various aspects of the method for minimizing fragmentation of the invention.

Turning to FIG. 1 there is shown a flowchart of the method of the present invention. This method can be performed on a computer running any operating system, including, but not limited to, Microsoft Windows 95®, Windows 98®, Windows ME®, Windows NT®, and Windows 2000® (Standard and Professional Edition) and all dialects of UNIX (such as IBM's AIX and Linux). The method can also be performed on a computer running any file system including, but not limited to, the FAT file system (including FAT32), NTFS, and the like. The computer readable medium can be a disk (such as a floppy disk, hard disk, ZIP disk, or Bernoulli disk), CD-RW, CD-R, or the like.

First, at least one of the available blocks in the computer readable medium or a selected portion of the computer readable medium is identified (step 102). An "available block" as used herein is one or more contiguous available clusters surrounded by unavailable clusters. Preferably, most, if not all, available blocks in the computer readable medium are identified.

Second, the size, location, or both of at least one and preferably at least two available blocks is determined (step 104). Preferably, the size and location are determined while identifying the available blocks. This information may be generated and stored in a free cluster list ("FCL"). At a minimum, the FCL generally contains the cluster ID of the first cluster in each available block and the number of subsequent clusters available in the block. For example, if cluster IDs 15–35 are available, the FCL would include the following entry:

| Starting Cluster ID | Number of Subsequent Clusters Available |
|---|---|
| 15 | 20 |

A request to allocate one or more clusters to a file (step 106) is received. The request may include the size of the clusters to be allocated as well as other parameters, such as the cluster IDs of the first, last, or all of the clusters allocated to the file if it already exists. Other such parameters include the file type, file name, and the cluster ID of the last cluster of the file (if it already exists).

Upon receiving such a request, a starting cluster location based on the size and/or location of the identified available blocks is determined. The starting cluster location is the beginning cluster location at which clusters will be sequentially allocated to the file. The starting cluster location is chosen by selecting an available block based on some criteria and then selecting a cluster within that block.

The available block may be chosen based on its size. For instance, the largest available block on the computer readable medium may be selected. The available block can also be selected based on the file type, file name, or both of the file for which the clusters are to be allocated. For example, all temporary or swap files can be stored near the end of the disk (i.e., at clusters having cluster IDs near the maximum cluster ID of the disk) or in remote areas of the disk.

Another method of selecting an available block is by estimating the size of the file (step 108). The size of the file can be estimated by any method known in the art. The size of the file can be estimated to be a predetermined size, such as, for example, 1 or 4 megabytes. The size can also be estimated to be the sum of a predetermined size, such as, for example, 1 or 4 megabytes, and the size of the space requested. The average size of the files on the computer readable medium can also be used as the estimated size.

Another method of estimating the size of the file is based on its file type and/or file name. For example, all ".doc" files (i.e. Microsoft Word® files) can be estimated to be 1 megabyte in size, while all ".mdb" files (i.e. Microsoft Access® files) can be estimated to be 4 megabytes in size. Optionally, the size of the file can be estimated to be the average file size of that file type. Temporary files, such as those which begin with "~" or end with ".tmp" in their file name, may be estimated to have a file size of zero in order to have them written in the first available block (i.e. the inner most block on the computer readable medium). Since many types of temporary files are rarely accessed, fragmentation of such files does not generally effect performance of the computer system.

For preexisting files where the request is to allocate additional clusters to the file, the size of the file may be estimated based on its current size and/or the size of the extension requested. For example, the estimated size of the file may be estimated to be a certain percentage of the sum of the current file size and the extension requested, such as 100% or 200%.

The probability of the file being extended in the future may also be used to estimate the size. The probability of the file being extended can be extrapolated from the type, name, and, if it is preexisting, prior longevity. For example, if the file has a high probability of being extended in the future, the estimated size may be 200% larger than the requested amount of space while if there is a low probability of such an extension, the estimated size may be 100% larger than the requested amount of space.

An available block is selected based on the estimated size, type, name, location, or combination thereof of the file and the size of at least one available block (step 110). For instance, an available block may be selected by comparing the estimated size of the file with the size of at least one available block so as to detect a block having an associated size which is greater than or equal to the estimated size. The comparison can be performed to detect the smallest or, alternatively, the first available block having an associated size which is greater than or equal to the estimated size. The comparison can also be performed to detect an available block which is not the first available block having an associated size greater than or equal to the estimated size. The comparison may alternatively be performed to detect a block having an associated size which is within a predetermined amount of the estimated size, such as, for example, within 10% of the estimated size of the block.

The comparison can also take into account the probability of files around each available block being extended. System files are unlikely to be extended, while database files are highly likely to be extended in the future. Thus, it would be preferable to select available blocks adjacent or near system files over those adjacent or near database files. Generally, It is preferable to select available blocks which have a low probability of the surrounding files being extended in order to reduce the likelihood of fragmentation of the surrounding files and the new file being stored.

The available block can also be selected by estimating the file's longevity based on the file type and/or name. For example, temporary files and swap files can be placed near the end of the disk, i.e., in clusters with cluster IDs close to the maximum cluster ID for the disk, so as to minimize storage of these files in frequently used areas of the disk.

Yet another method of selecting an available block is to compare the location of at least one available block with a predetermined location on the computer readable medium in order to select the available block closest to the predetermined location. For example, the available block physically closest to the last cluster allocated can be selected. The starting cluster location may also be determined based on the closest available block which has a size greater than or equal to an estimated size of the file or based on the current physical position of the drive head.

When a request to extend a preexisting file is received, the available block physically closest to the clusters allocated to the preexisting file can be selected. The starting cluster location may be determined based on the location of any of the clusters allocated to the preexisting file, such as the last cluster allocated to the preexisting file. The starting cluster location may also be determined based on the location of the largest allocated block for the preexisting file. Unlike the prior art method, which only searches for the first available cluster after the last cluster allocated to a file, the method of the present invention can determine the closest available cluster before or after the clusters allocated to the preexisting file.

Once an available block has been selected, a starting cluster location within that block is selected. The starting cluster location can be anywhere, i.e., at any cluster, in the selected available block. Typically, the first cluster in the available block, i.e., the cluster having the lowest cluster ID in the available block, is selected to be the starting cluster location. The starting cluster location can also be a cluster in the available block other than the first cluster.

In some circumstances, it may be advantageous to select a starting cluster location several clusters after the first cluster in the available block, e.g., when there is a high probability that a file allocated to one or more clusters before the available block will be extended in the future. In such a situation, the starting cluster location can be determined by estimating the size of the extended file and selecting a starting cluster location which leaves enough space for the preexisting file to be extended. The probability of a file being extended can be determined based on its longevity and last modification date.

Thereafter, the clusters can be allocated beginning at the starting cluster location (step 112). The newly allocated clusters can then be identified as being unavailable, such as by modifying the FCL (step 114).

Figure 2:
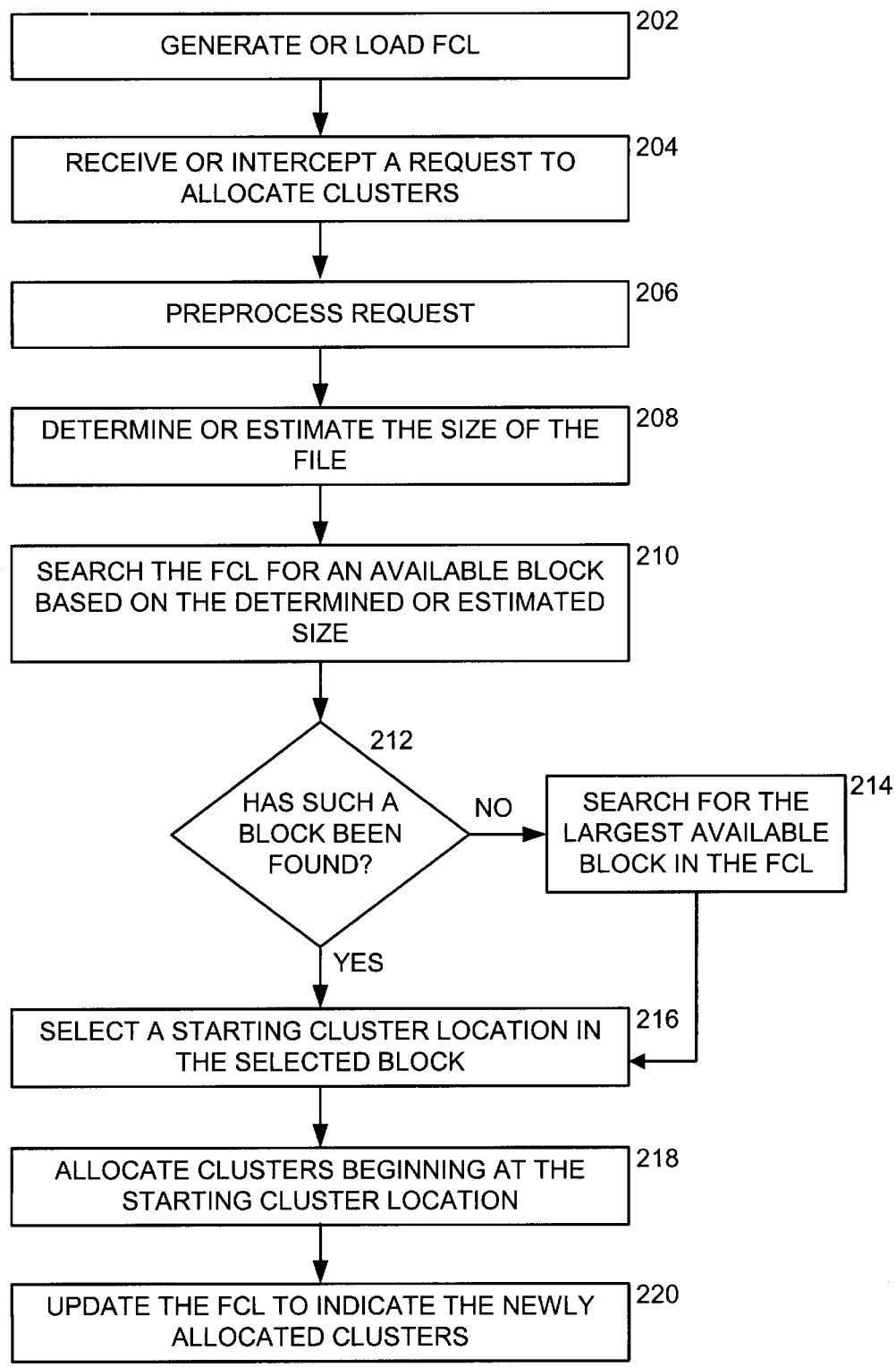
FIG. 2 is a flow chart of one embodiment of the method for minimizing fragmentation of the invention.

FIG. 2 illustrates another embodiment of the method of the present invention. During boot up of the computer, a driver is loaded which generates or loads a FCL of all available clusters on the disk (step 202). If the FCL is loaded at boot up, the FCL is preferably stored before the computer system is shut down. A flag or semaphore may be used to maintain the integrity of the FCL in such an embodiment. Alternatively, the FCL may be built from the allocation table for the disk during boot up.

Also during boot up, the other routines for allocating and freeing clusters are loaded. These drivers may include the features of the present invention. Alternatively, the routines of the file system may be intercepted or redirected to secondary routines which include the features of the present invention.

According to one preferred embodiment, the drivers of Microsoft Windows 95®, Windows 98®, or Windows ME® are intercepted or redirected to such secondary routines. In Microsoft Windows 95®, Windows 98®, and Windows ME®, the routine for allocating clusters to a file or directory (hereinafter referred to as "AllocCluster") is located in the vfat.vxd driver (which is loaded by the vmm32.vxd driver during boot up).

The AllocCluster routine receives various parameters from the program which calls it, including the last allocated cluster (stored in the variable "ClusAlloc"), the volume (or logical drive) structure on which clusters are to be allocated, the number of clusters requested, and the open file structure which includes the entire location of the file if it exists, the existing size, and last date modified. The routine also receives the last cluster of the file if it exists. If the file does not exist, the last cluster variable is set to zero.

After AllocCluster is loaded into the random access memory of the computer, a second driver (hereinafter referred to as "the Alloc intercept routine" ) is loaded. The memory location or locations assigned to the AllocCluster routine are then altered to refer to the Alloc intercept routine. Thus, when a program calls the AllocCluster routine, the Alloc intercept routine is executed instead of the AllocCluster routine.

In an alternative embodiment, the request is intercepted by replacing the AllocCluster routine in memory with a stub routine which calls the intercept routine. The AllocCluster routine may optionally be moved to another location in memory.

In Microsoft Windows 95® and Windows 98® systems, a routine (hereinafter referred to as "SetFATEntry") is called whenever a cluster value is set, i.e., whenever a cluster is allocated or freed. This routine modifies the allocation table to correctly indicate newly allocated or freed clusters. The SetFATEntry routine is intercepted by the method described above and redirected to a routine hereinafter called "the SetFAT intercept routine". Whenever the SetFAT intercept routine is called, the allocation table and FCL are both updated. For example, if cluster IDs 5–10 and 15–20 were previously available, and a file which is located at cluster IDs 11–14 has been deleted, the FCL would be modified from:

| Starting Cluster ID | Number of Subsequent Clusters Available |
| --- | --- |
| 5 | 5 |
| 15 | 5 | to:

| Starting Cluster ID | Number of Subsequent Clusters Available |
| --- | --- |
| 5 | 15 |

Microsoft Windows 95® and Windows 98® further include a routine known as ExecInt located in the vmm.vxd driver which simulates software interrupts including DOS interrupts that lock and unlock the disk, volume, or other logical drive so that other programs cannot allocate or free clusters. When an application program, such as a disk utility, requests that a software interrupt be generated, the request is channeled to ExecInt. For example, the disk can be locked so that defragmentation programs and other disk utility programs can perform their tasks safely without other programs interfering. This routine is also intercepted or redirected to a routine hereinafter called ExecInt intercept routine. Since defragmentation programs and other disk utilities frequently directly access the allocation table of a disk without executing the AllocCluster or the SetFatEntry routines, the ExecInt intercept routine rebuilds the FCL after the disk is unlocked and disables the intercept routines of the present invention (except the ExecInt intercept routine), while the disk is locked.

A file system API hook is also installed so it can receive notifications whenever a disk volume is mounted (activated) by the system. When a disk volume is mounted, the system API hook generates or calls a routine to generate the FCL for that volume.

When a request to allocate clusters is received (whether it is intercepted, redirected, or directly processed) (step 204), the request may be preprocessed (step 206). During this preprocess step, it can be determined whether a simple heuristic, such as that known in the prior art, or the heuristic of the present invention should be used to allocate clusters. For example, if the clusters to be allocated are for a preexisting file or a new temporary file (step 206), the clusters may be allocated based on the prior art method described above. In such circumstances, the intercept routine can pass the request to the prior handler (i.e. the routine which was initially called) for processing.

Assuming the clusters have not been allocated during the preprocess step, the size of the file or the extension to the file for which clusters are to be allocated is determined or estimated (step 208). The size of the file can be estimated by any of the aforementioned methods. According to a preferred embodiment, the size of the file is estimated to be the sum of a predetermined size, such as, for example, 1 or 4 megabytes, and the size of the space requested.

Once the size of the file or the extension to the file has been estimated, the FCL is searched for a block of contiguous free clusters which is greater than or equal to that size (step 210). The FCL may be searched randomly or based on some additional criteria. According to one embodiment, the FCL is searched based on the cluster ID, beginning at cluster ID 1, i.e., the FCL is searched for the first available block of contiguous free clusters which has a size greater than or equal to the estimated size.

According to another embodiment, the FCL is searched for a block of contiguous free clusters which has a size within a fixed percentage, such as 10%, of the estimated size.

The FCL may also be searched for an available block closest to a physical location on the computer readable medium, which has a size greater than or equal to the estimated size. For example, for an existing file which is to be extended, the FCL may be searched for the available block closest to the clusters currently allocated to the file, which is greater than or equal to the estimated size.

If a block of contiguous clusters matching these criteria is not found (step 212), a search may be performed with different criteria, such as searching for the largest available block of contiguous clusters in the FCL (step 214). Both searches may be performed in a single traverse of the FCL by methods known in the art.

If no available block is found matching any of the criteria used, the clusters may be allocated according to any existing heuristic previously known, such as that described above.

Once an available block is found, a starting cluster location is chosen residing in the available block (step 216). The first cluster in the available block is typically chosen to be the starting cluster location. Thereafter, the clusters requested are allocated beginning at the starting cluster location in the block (step 218). The clusters may be allocated by simply calling the Alloc Cluster routine with the ClusAlloc variable set to one less than the cluster ID of the starting cluster location, i.e., (Cluster ID)$_{Starting\ Cluster\ Location}$ −1. The FCL is then updated to indicate the newly allocated clusters (step 220).

Figure 3:
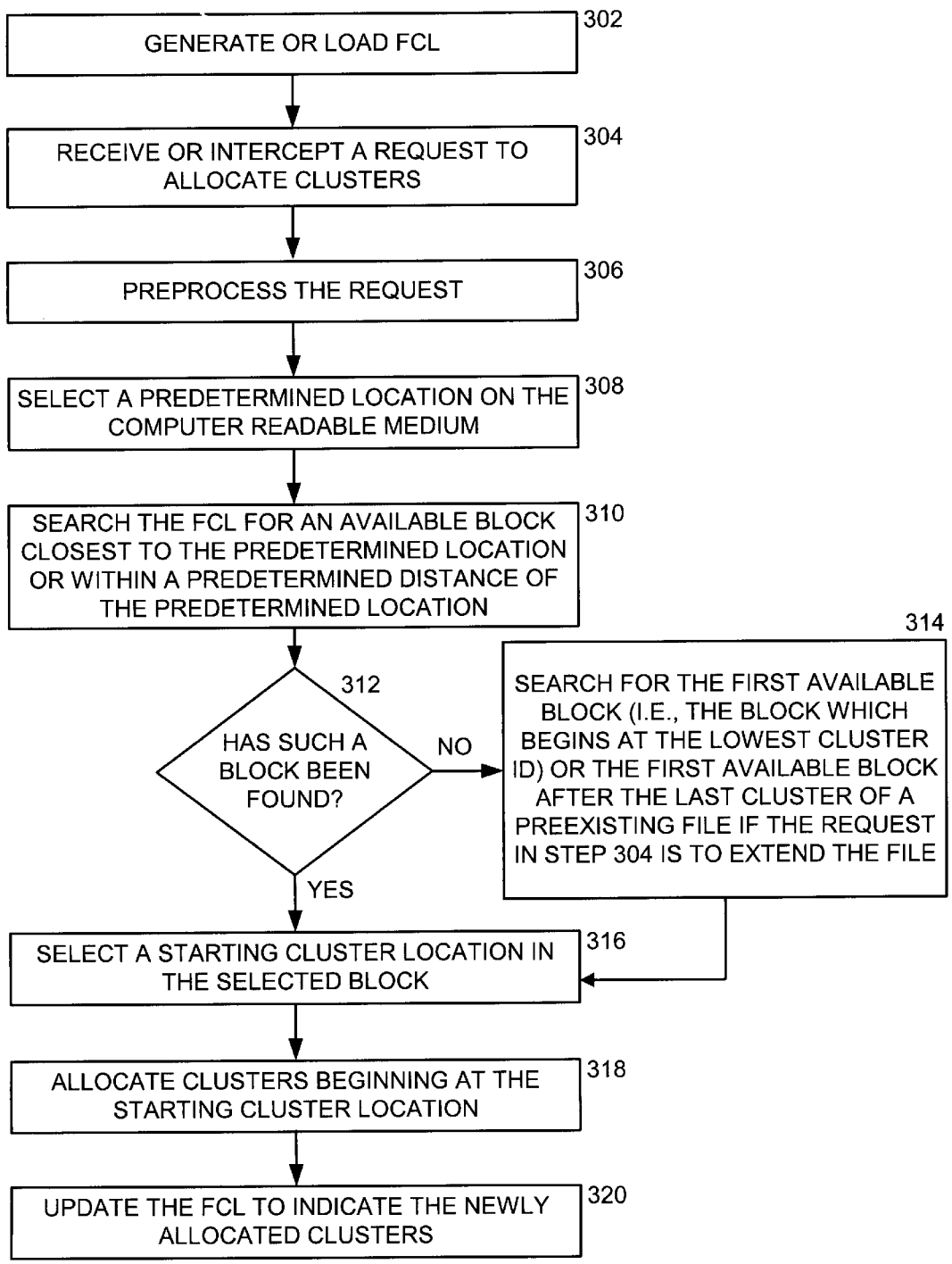
FIG. 3 is a flow chart of another embodiment of the method for minimizing fragmentation of the invention.

Another embodiment of the present invention is shown in FIG. 3. First, a FCL is generated or loaded (step 302). When a request to allocate clusters is received (whether it is intercepted, redirected, or directly processed) (step 304), the request may be preprocessed (step 306) as described above. Assuming the clusters have not been allocated during the preprocess step, a predetermined location on the computer readable medium is selected (step 308). The FCL is searched for the available block closest to or a predetermined distance away from the predetermined location on the computer readable medium (step 310). If a block matching the criteria is not found (step 312), a search may be performed with different criteria or by any other method known in the prior art, such as that described above (step 314).

Once an available block has been chosen, a starting cluster location within the available block is selected by any of the aforementioned methods (step 316). Thereafter, the clusters requested are allocated beginning at the starting cluster location in the block (step 318) and the FCL is updated to indicate the newly allocated clusters (step 320).

A preferred embodiment of the invention is shown in FIG. 4. After a request is received to allocate clusters to a file (step 402), such as to AllocCluster, the request is intercepted (step 404). The Alloc intercept routine then preprocesses the request (step 406). If the request fails the criteria set out in the preprocess step, the request is redirected to AllocCluster, which will allocate the clusters according to the method known in the prior art. The criteria may include the file type. For example, if the request is to extend a preexisting file or allocate clusters for a temporary file, the request may be returned to AllocCluster (step 408).

Assuming the request passes the preprocess step, the size of the file is estimated (step 410) and the FCL is searched for an available block (steps 412, 414, 416, and 418) by any of the aforementioned methods. The clusters are then allocated within the available block, preferably beginning at the first cluster of the block found (step 420). The clusters may be allocated by calling AllocCluster and providing the starting cluster location (preferably the first cluster of the block found).

While there have been shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

What is claimed is:

1. A method of allocating clusters of a computer readable medium containing a plurality of clusters to a file while minimizing fragmentation of the computer readable medium, the method comprising the steps of:
   (a) identifying at least one available block in the computer readable medium, each block including one or more contiguous available clusters;
   (b) determining the size, location, or both of at least one of the identified available blocks;
   (c) receiving a request to allocate one or more clusters to a file;
   (d) determining a starting cluster location based on the size of at least one of the identified available blocks, the location of at least one of the identified available blocks, or both; and
   (e) allocating the clusters requested beginning at the starting cluster location,
wherein each cluster comprises one or more units of storage space and the starting cluster location is not determined from only the location of one available block.

2. The method of claim 1, wherein the computer readable medium is a disk.

3. The method of claim 1, wherein steps (a) and (b) are performed concurrently.

4. The method of claim 1, wherein step (b) comprises determining the size, location, or both of at least two of the identified available blocks.

5. The method of claim 1, wherein step (d) is performed after steps (a) and (b).

6. The method of claim 1, wherein step (c) is performed after steps (a) and (b).

7. The method of claim 1, wherein the request in step (c) provides the file name, file type, or both.

8. The method of claim 1, wherein the request in step (c) provides the location of the first, last, or all the clusters of the file if the file preexists.

9. The method of claim 1, wherein step (c) comprises intercepting a request to allocate one or more clusters to a file.

10. The method of claim 1, wherein step (d) comprises
   (i) identifying the largest available block on the computer readable medium; and
   (ii) selecting a starting cluster location within the largest available block.

11. The method of claim 10, wherein the starting cluster location is the first cluster in the largest available block.

12. The method of claim 1, wherein step (d) comprises
   (i) determining the type, name, location, or combination thereof of the file; and
   (ii) determining a starting cluster location based on the type, name, location, or combination thereof of the file.

13. The method of claim 1, wherein step (d) comprises
   (i) estimating the size of the file; and
   (ii) determining a starting cluster location based on the estimated size of the file and the size of at least one available block.

14. The method of claim 13, wherein step (d)(i) comprises estimating that the size of the file is a predetermined size or the sum of a predetermined size and the size of the clusters requested.

15. The method of claim 14, wherein the predetermined size is 1 or 4 megabytes.

16. The method of claim 13, wherein step (d)(i) comprises determining the average size of a file on the computer readable medium and estimating that the size of the file is the average size.

17. The method of claim 13, wherein the request in step (c) provides the file name, file type, or both; and step (d)(i) comprises estimating the size of the file based on the file type, file name, or both.

18. The method of claim 17, wherein step (d)(i) comprising identifying a temporary file based on the file type, file name, or both; and estimating the size of the temporary file as zero.

19. The method of claim 13, wherein step (d)(ii) comprises (A) comparing the estimated size of the file with the size of at least one available block so as to detect an available block having an associated size which is greater than or equal to the estimated size; and (B) selecting a starting cluster location within the detected block.

20. The method of claim 19, wherein step (d)(ii)(A) comprises comparing the estimated size of the file with the size of at least one available block so as to detect the first available block having an associated size which is greater than or equal to the estimated size.

21. The method of claim 19, wherein step (d)(ii)(A) comprises comparing the estimated size of the file with the size of at least one available block so as to detect the smallest available block having an associated size which is greater than or equal to the estimated size.

22. The method of claim 19, wherein the selected starting cluster location is the first cluster in the detected block.

23. The method of claim 19, wherein the selected starting cluster location is not the first cluster in the detected block.

24. The method of claim 1, wherein step (d) comprises
   (i) identifying a location on the computer readable medium; and
   (ii) determining a starting cluster location based on the identified location.

25. The method of claim 24, wherein the request in step (c) provides the file name, file type, or both; and step (d)(i) comprises identifying a location on the computer readable medium based on the file type, file name, or both.

26. The method of claim 25, wherein the file is a temporary file.

27. The method of claim 25, wherein the identified location in step (d)(i) is the last cluster accessed.

28. The method of claim 24, wherein step (d)(ii) comprises comparing the identified location with the location of at least one available block so as to detect the available block closest to the identified location; and selecting a starting cluster location within the detected block.

29. The method of claim 28, wherein the file exists before the request is received and the identified location in step (d)(i) is the last cluster of the existing file.

30. The method of claim 28, wherein the identified location is the last cluster accessed.

31. The method of claim 30, wherein the selected starting cluster location is the first cluster in the detected block.

32. The method of claim 1, wherein step (d) comprises
   (i) estimating the size of the file;
   (ii) identifying a location on the computer readable medium; and
   (ii) determining a starting cluster location based on the estimated size of the file, the identified location, and the size and location of at least one available block.

33. The method of claim 32, wherein step (d)(iii) comprises comparing the estimated size of the file with the size of at least one available block and the identified location with the location of at least one available block so as to detect the available block closest to the identified location which has an associated size which is greater than or equal to the estimated size; and selecting a starting cluster location within the detected block.

34. The method of claim 33, wherein the selected starting cluster location is the first cluster in the detected block.

35. The method of claim 33, wherein the selected starting cluster location is not the first cluster in the detected block.

36. The method of claim 1, further comprising the step of:
   (f) identifying the allocated clusters as being unavailable.

37. A computer-readable medium containing a software program that includes instructions for performing the method in claim 1.

38. A computer-readable medium containing a software program that includes instructions for performing the method in claim 13.

39. A method of allocating clusters of a computer readable medium containing a plurality of clusters to a file while minimizing fragmentation of the computer readable medium, the method comprising the steps of:
   (a) identifying at least one available block in the computer readable medium, each block including one or more contiguous available clusters;
   (b) determining the size, location, or both of at least one of the identified available blocks;
   (c) receiving a request to allocate one or more clusters to a file;
   (d) identifying the largest available block on the computer readable medium;
   (e) selecting a starting cluster location within the largest available block; and
   (f) allocating the clusters requested beginning at the starting cluster location, wherein each cluster comprises one or more units of storage space.

40. The method of claim 39, wherein the starting cluster location is the first cluster in the largest available block.

41. A method of allocating clusters of a computer readable medium containing a plurality of clusters to a file while minimizing fragmentation of the computer readable medium, the method comprising the steps of:
  (a) identifying at least one available block in the computer readable medium, each block including one or more contiguous available clusters;
  (b) determining the size, location, or both of at least one of the identified available blocks;
  (c) receiving a request to allocate one or more clusters to a file;
  (d) determining the type, name, location, or combination thereof of the file;
  (e) determining a starting cluster location based on (i) the type, name, location, or combination thereof of the file and (ii) the size of at least one of the identified available blocks, the location of at least one of the identified available blocks, or both; and
  (f) allocating the clusters requested beginning at the starting cluster location,
wherein each cluster comprises one or more units of storage space.

42. A method of allocating clusters of a computer readable medium containing a plurality of clusters to a file while minimizing fragmentation of the computer readable medium, the method comprising the steps of:
  (a) identifying at least one available block in the computer readable medium, each block including one or more contiguous available clusters;
  (b) determining the size, location, or both of at least one of the identified available blocks;
  (c) receiving a request to allocate one or more clusters to a file;
  (d) estimating the size of the file;
  (e) determining a starting cluster location based on the estimated size of the file and the size of at least one available block; and
  (f) allocating the clusters requested beginning at the starting cluster location,
wherein each cluster comprises one or more units of storage space.

43. The method of claim 42, wherein step (d) comprises estimating that the size of the file is a predetermined size or the sum of a predetermined size and the size of the clusters requested.

44. The method of claim 43, wherein the predetermined size is 1 or 4 megabytes.

45. The method of claim 42, wherein step (d) comprises determining the average size of a file on the computer readable medium and estimating that the size of the file is the average size.

46. The method of claim 42, wherein the request in step (c) provides the file name, file type, or both; and step (d) comprises estimating the size of the file based on the file type, file name, or both.

47. The method of claim 46, wherein step (d) comprising identifying a temporary file based on the file type, file name, or both; and estimating the size of the temporary file as zero.

48. The method of claim 42, wherein step (e) comprises (i) comparing the estimated size of the file with the size of at least one available block so as to detect an available block having an associated size which is greater than or equal to the estimated size; and (ii) selecting a starting cluster location within the detected block.

49. The method of claim 48, wherein step (e)(i) comprises comparing the estimated size of the file with the size of at least one available block so as to detect the first available block having an associated size which is greater than or equal to the estimated size.

50. The method of claim 48, wherein step (e)(i) comprises comparing the estimated size of the file with the size of at least one available block so as to detect the smallest available block having an associated size which is greater than or equal to the estimated size.

51. The method of claim 48, wherein the selected starting cluster location is the first cluster in the detected block.

52. The method of claim 48, wherein the selected starting cluster location is not the first cluster in the detected block.

53. A method of allocating clusters of a computer readable medium containing a plurality of clusters to a file while minimizing fragmentation of the computer readable medium, the method comprising the steps of:
  (a) identifying at least one available block in the computer readable medium, each block including one or more contiguous available clusters;
  (b) determining the size, location, or both of at least one of the identified available blocks;
  (c) receiving a request to allocate one or more clusters to a file;
  (d) identifying a location on the computer readable medium;
  (e) determining a starting cluster location based on (i) the identified location and (ii) the location of at least one of the identified available blocks; and
  (f) allocating the clusters requested beginning at the starting cluster location,
wherein each cluster comprises one or more units of storage space.

54. The method of claim 53, wherein the request in step (c) provides the file name, file type, or both; and step (d) comprises identifying a location on the computer readable medium based on the file type, file name, or both.

55. The method of claim 54, wherein the file is a temporary file.

56. The method of claim 54, wherein the identified location in step (d) is the last cluster accessed.

57. The method of claim 53, wherein step (e) comprises comparing the identified location with the location of at least one available block so as to detect the available block closest to the identified location; and selecting a starting cluster location within the detected block.

58. The method of claim 57, wherein the file exists before the request is received and the identified location in step (d) is the last cluster of the existing file.

59. The method of claim 57, wherein the identified location is the last cluster accessed.

60. The method of claim 59, wherein the selected starting cluster location is the first cluster in the detected block.

61. A computer system comprising:
  (a) a computer readable medium having a plurality of clusters;
  (b) a processor in communication with the computer readable medium, the processor configured to:
    (i) identify at least one available block in the computer readable medium, each block including one or more contiguous available clusters;
    (ii) determine the size, location, or both of at least one of the available block;

(iii) receive a request to allocate one or more clusters to a file;

(iv) determine a starting cluster location based on the size of at least one identified available block, location of at least one identified available block, or both; and (v) allocate the clusters requested beginning at the starting cluster location.

62. A method of allocating clusters of a computer readable medium containing a plurality of clusters to a file while minimizing fragmentation of the computer readable medium, the method comprising the steps of:

(a) identifying at least one available block in the computer readable medium, each block including one or more contiguous available clusters;

(b) determining the size and location of at least one available block, the size of the available block representing the number of contiguous available clusters;

(c) intercepting a request to allocate one or more clusters to a file;

(d) estimating the size of the file;

(e) determining a starting cluster location based on the estimated size of the file and the size of at least one available block; and (f) allocating the clusters requested beginning at the starting cluster location, wherein each cluster comprises one or more units of storage space.

63. A method of allocating clusters of a computer readable medium containing a plurality of clusters to a file while minimizing fragmentation of the computer readable medium, the method comprising the steps of:

(a) identifying at least one available block in the computer readable medium, each block including one or more contiguous available clusters;

(b) determining the size, location, or both of at least one of the identified available blocks;

(c) intercepting a request to a Windows operating system routine to allocate one or more clusters to a file;

(d) determining a starting cluster location based on the size of at least one of the identified available blocks, the location of at least one of the identified available blocks, or both; and (e) sending a request to the Windows operating system routine to allocate one or more clusters to the file beginning at the starting cluster location, wherein each cluster comprises one or more units of storage space and the file system of the computer readable medium is FAT or FAT32.

64. A method of allocating clusters of a computer readable medium containing a plurality of clusters to a file while minimizing fragmentation of the computer readable medium, the method comprising:

at boot up, identifying at least one available block in the computer readable medium, each block including one or more contiguous available clusters;

at boot up, determining the size, location, or both of at least one of the identified available blocks;

at boot up, receiving a request to allocate one or more clusters to a file;

at boot up, determining a starting cluster location based on the size of at least one of the identified available blocks, the location of at least one of the identified available blocks, or both; and at boot up, allocating the clusters requested beginning at the starting cluster location, wherein each cluster comprises one or more units of storage space and the starting cluster location is not determined from only the location of one available block.

65. The method of claim 64, further comprising estimating a size of the file, and determining a starting cluster location based on the estimated size of the file.

66. The method of claim 65, wherein the size of the file is estimated based on at least one of the file name and file type.

67. The method of claim 65, wherein the size of the file is estimated based at least in part on a probability of the file being extended in the future.

68. A computer-readable medium containing a software program that includes instructions for performing the method in claim 64.

69. A method of allocating clusters of a computer readable medium containing a plurality of clusters to a file while minimizing fragmentation of the computer readable medium, the method comprising:

identifying at least one available block in the computer readable medium, each block including one or more contiguous available clusters, wherein each cluster comprises one or more units of storage space;

receiving a request to allocate one or more clusters to a file;

selecting at least one of the available blocks based on a location of the available block;

allocating at least some of the clusters in the selected blocks to the file; and writing the file to the allocated clusters.

70. The method of claim 69, further comprising determining a size of the file, and wherein at least one of the available blocks is further selected based on the size of the file.

71. A computer-readable medium containing a software program that includes instructions for performing the method in claim 69.

* * * * *